US008295947B2

(12) United States Patent
Lamson et al.

(10) Patent No.: US 8,295,947 B2
(45) Date of Patent: *Oct. 23, 2012

(54) DEVICES AND METHODS FOR TRANSLUMINAL OR TRANSTHORACIC INTERSTITIAL ELECTRODE PLACEMENT

(75) Inventors: Theodore C. Lamson, Pleasanton, CA (US); Joshua Makower, Los Altos, CA (US); J. Christopher Flaherty, Topsfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1006 days.

This patent is subject to a terminal disclaimer.

(21) Appl. No.: 11/591,295

(22) Filed: Oct. 31, 2006

(65) Prior Publication Data

US 2007/0100410 A1    May 3, 2007

Related U.S. Application Data

(63) Continuation of application No. 10/411,891, filed on Apr. 11, 2003, now Pat. No. 7,191,015.

(60) Provisional application No. 60/371,742, filed on Apr. 11, 2002.

(51) Int. Cl.
*A61N 1/05* (2006.01)

(52) U.S. Cl. ......... 607/119; 607/126; 607/129; 607/130

(58) Field of Classification Search .................. 607/119, 607/122, 129–132; 606/129
See application file for complete search history.

(56) References Cited

U.S. PATENT DOCUMENTS

| 4,378,023 A | * | 3/1983 | Trabucco ...................... 607/128 |
|---|---|---|---|
| 4,497,326 A | | 2/1985 | Curry |
| 4,991,578 A | * | 2/1991 | Cohen ................................ 607/2 |
| 5,033,477 A | | 7/1991 | Chin et al. |
| 5,336,252 A | | 8/1994 | Cohen |
| 5,383,924 A | | 1/1995 | Brehier |
| 5,588,432 A | * | 12/1996 | Crowley ........................ 600/439 |
| 5,755,760 A | * | 5/1998 | Maguire et al. ................ 607/122 |
| 5,823,956 A | * | 10/1998 | Roth et al. ...................... 600/374 |
| 5,830,222 A | | 11/1998 | Makower |
| 5,902,331 A | * | 5/1999 | Bonner et al. ................. 607/122 |
| 5,968,010 A | * | 10/1999 | Waxman et al. ............... 600/500 |
| 6,068,638 A | | 5/2000 | Makower |
| 6,071,292 A | | 6/2000 | Makower et al. |
| 6,190,353 B1 | | 2/2001 | Makower et al. |
| 6,200,303 B1 | | 3/2001 | Verrior et al. |
| 6,375,615 B1 | | 4/2002 | Flaherty et al. |
| 6,535,764 B2 | | 3/2003 | Imran et al. |

(Continued)

FOREIGN PATENT DOCUMENTS

WO    WO 99/49793    10/1999

(Continued)

*Primary Examiner* — Niketa Patel
*Assistant Examiner* — Hiba El-Kaissi

(57) ABSTRACT

Methods and devices for implanting pacing electrodes or other apparatus, or for delivering substances, to the heart of other tissues within the body. A guided tissue penetrating catheter is inserted into a body lumen (e.g., blood vessel) or into a body cavity or space (e.g., the pericardial space) and a penetrator is advanced from the catheter to a target location. In some embodiments, a substance or an apparatus (such as an electrode) may be delivered through a lumen in the penetrator. In other embodiments, a guidewire may be advanced through the penetrator, the penetrating catheter may then be removed and an apparatus (e.g., electrode) may then be advanced over that guidewire. Also disclosed are various implantable electrodes and electrode anchoring apparatus.

15 Claims, 10 Drawing Sheets

U.S. PATENT DOCUMENTS

| | | |
|---|---|---|
| 6,544,230 B1 | 4/2003 | Flaherty et al. |
| 6,561,998 B1 | 5/2003 | Roth et al. |
| 2002/0111619 A1 | 8/2002 | Keast et al. |
| 2002/0165535 A1 | 11/2002 | Lesh et al. |
| 2003/0109809 A1 | 6/2003 | Jen et al. |
| 2003/0212446 A1 | 11/2003 | Kaplan et al. |

FOREIGN PATENT DOCUMENTS

| | | | |
|---|---|---|---|
| WO | WO 99/49910 | * | 10/1999 |
| WO | WO99/49910 | * | 10/1999 |
| WO | WO 02/062265 | | 8/2002 |

* cited by examiner

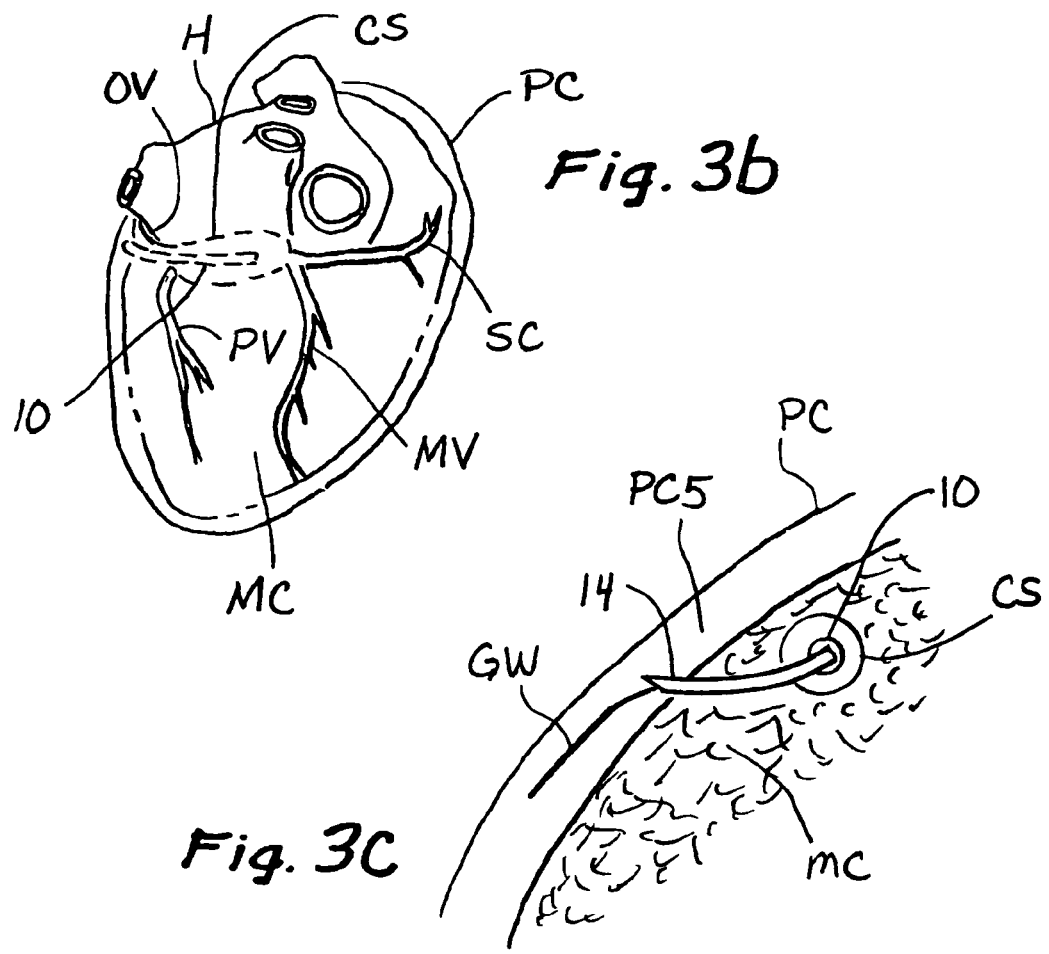
Fig. 3b
Fig. 3C
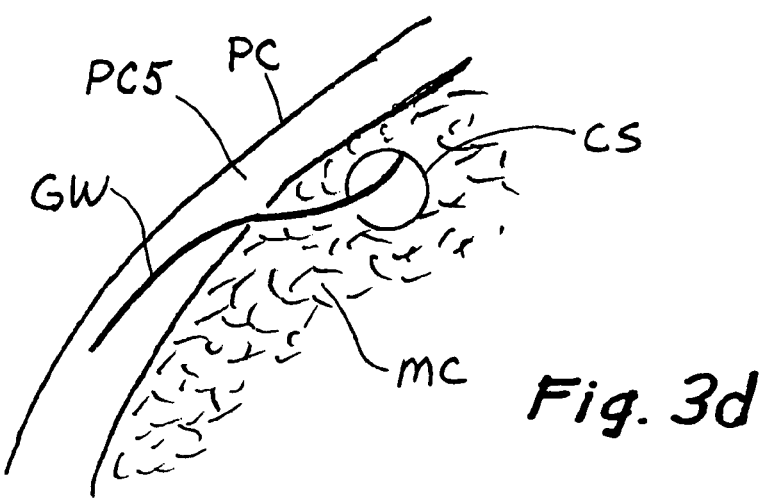
Fig. 3d

DEVICES AND METHODS FOR TRANSLUMINAL OR TRANSTHORACIC INTERSTITIAL ELECTRODE PLACEMENT

RELATED APPLICATIONS

This patent application is a continuation of co-pending U.S. patent application Ser. No. 10/411,891 filed Apr. 11, 2003 now issued as U.S. Pat. No. 7,191,015, which claims priority to U.S. Provisional Patent Application No. 60/371, 742 filed on Apr. 11, 2002, the entire disclosures of which are expressly incorporated herein by reference.

BACKGROUND OF THE INVENTION

There exist numerous situations in which it is desirable to implant or position electrodes at specific locations within the body. In some situations it is desirable to pass electrodes into the body through blood vessels or other body lumens in order to position the electrode in or near an organ or portion of the body that would otherwise be accessed only by open surgical means. However, allowing an electrode to remained positioned within a blood vessel or other body lumen may, in at least some cases, be less than desirable. Accordingly, there exists a need in the art for devices and methods to facilitate advancement of an electrode through a body lumen to a location near the tissue or organ in which the electrode is to be placed and, thereafter, to cause the electrode to travel outside of that body lumen in into the desired tissue or organ parenchyma. The present invention satisfies such need.

One of the many applications in which transluminal/interstitial electrode placement is desirable is for placing pacing electrodes within myocardial tissue. At present, it is common for physicians to transvenously insert pacing wires into coronary veins for the purpose of treating cardiac rhythm disturbances. This allows the electrode to float freely in the coronary vein and the electrode does not become interstitially implanted within myocardial tissue. Recently, a technique known as "cardiac resynchronization therapy" (CRT) has been used for the treatment of congestive heart failure. CRT involves pacing of both left and right ventricles to enhance the heart's pumping efficiency. In a recent 12-month study conducted in Europe and Canada, it was concluded that the administration of CRT using the Medtronic InSync® system resulted in decreased fatigue and increased exercise tolerance for as long as one year following CRT.

In general, CRT utilizes an implantable pacemaker-like device that delivers electrical impulses to resynchronize the beating action of the heart's chambers. This implantable pacemaker-like device is implanted subcutaneously in the pectoral area. Two (2) endocardial leads which are placed in the right atrium and right ventricle and a third epicardial lead is placed transvenously within a coronary vein located on the outside of the left ventricle. It has heretofore been the practice to allow the epicardial pacing lead (i.e., a wire having an electrode at its distal tip) to float freely within the lumen of a coronary vein located on or near the epicardial surface of the left ventricle. However, the use of such free-floating epicardial pacing electrode can be less than advantageous because a) the electrode can migrate or move through the lumen of the coronary vein b) the electrical pacing impulses delivered by that epicardial lead must be sufficiently strong to pass through the wall of the coronary vein and through adjacent myocardial tissue to reach the area within the myocardium where the impulse actually causes the desired myocardial muscle fibers to contract and c) where the electrode can be placed within the venous anatomy intraluminally may not be the most optimal myocardial location for electrical stimulation. If this epicardial electrode were to be positioned within the myocardial tissue at or near its intended site of action, instead of in the lumen of a coronary vein, the potential for migration of the electrode and the amount of current required to be delivered through the electrode would be minimized.

In addition, there exists a technique known as "neuromodulation" (NMT), in which electrodes are placed into areas of the brain and connected to permanently implantable stimulators. MNT has been used to treat disorders such as spasticity, pain, epilepsy and Parkinson's disease as well as several other neurological conditions. Other organs in which the transluminal/interstitial electrode placement of the present invention may have benefit include but are not limited to the gastrointestinal tract, kidney, carotid body or other vascular structures, bladder, skeletal muscle, spinal cord, nerves, respiratory tract, olfactory apparatus and the eye.

SUMMARY OF THE INVENTION

The present invention provides methods and devices for implanting or positioning pacing electrodes or other apparatus (e.g., guidewires, other types of electrodes, sensors, etc.) or injecting substances (e.g., drugs, cells, vectors, agents, biological factors, proteins, etc.) onto or into the heart of a human or veterinary patient.

In accordance with one embodiment of the invention, there is provided a method for implanting an apparatus (e.g., an electrode, sensor or other apparatus) at some interstitial location (e.g., within the myocardium of a patient's heart). In this method, a tissue penetrating catheter is initially advanced into a blood vessel or other body lumen. The tissue penetrating catheter comprises i) an elongate catheter body, ii) a hollow tissue penertator advanceable from the catheter body and iii) an orientation element useable to pre-determine the specific trajectory or direction in which the penetrator will advance from the catheter body is positioned within a blood vessel or other anatomical conduit (e.g., a coronary vein, coronary artery, coronary sinus). The catheter's orientation element is then used to position and rotationally orient the catheter within the blood vessel or body lumen such that, when the penetration is subsequently advanced, the penetration will enter the intended location where the apparatus is to be placed and/or where a substance is to be delivered. Thereafter, the apparatus is advanced into the desired interstitial location by one of the following techniques:

i) advancing a pacing electrode through the lumen of the penetration and into the intended extravascular location; or, ii) advancing a guidewire through the penetration and into the intended extravascular location and, thereafter, advancing the pacing electrode over the guidewire and into the intended implantation location; or, iii) advancing a guidewire through the penetration and into the intended extravascular location, advancing a tract enlarging apparatus over the guidewire and using the tract enlarging apparatus to enlarge the tract created by the penetration and/or the guidewire and, thereafter, advancing the pacing electrode over the guidewire and through the enlarged penetration tract to the intended implantation location.

Further in accordance with the invention, there is provided an electrode implantation system which comprises; i) an implantable anchoring member in combination with ii) an elongate, transluminally insertable electrode member that is insertable through a body lumen and into the anchoring member such that the anchoring member resists undesired movement or extraction of the electrode member. The anchoring member may be of any suitable design which engages the tissue so as to hold the electrode in a substantially fixed position. In some but not necessarily all embodiments, the implantable anchoring member may be resorbable or biodegradable. Also, in some but not necessarily all embodiments, the electrode member may be disengageable from the expanded anchoring member to permit the electrode member to be removed leaving the expanded anchoring member in place.

Still further in accordance with the invention there is provided a transluminal method for inserting a working apparatus (e.g., a guidewire, electrode, sensor, etc) into the pericardial space in a human or veterinary patient. In this method, a tissue penetrating catheter that comprises i) an elongate catheter body, ii) a hollow tissue penertator advanceable from the catheter body and iii) an orientation element useable to pre-determine the specific trajectory or direction in which the penetration will advance from the catheter body, is advanced into the cardiac vasculature (e.g., into the coronary sinus, coronary vein or a coronary artery). Thereafter, the catheter's orientation element is used to position the catheter such that when the penetration is subsequently advanced from the catheter the penetration will penetrate into the pericardial space. After the catheter has been so positioned and oriented, the penetration is advanced into the pericardial space and the working apparatus is then advanced through the hollow penetration and into the pericardial space. In embodiments where this working apparatus is a guidewire, the penetrating catheter may then be removed, leaving the guidewire within the pericardial space. The penetrating catheter may then be readvanced over this guidewire and into the pericardial space where it may be used to penetrate to a desire location within the heart and to introduce a second working apparatus (e.g., an electrode) into the heart. Alternatively, a second working apparatus (e.g., anchorable electrode) may be advanced directly over the guidewire and into the pericardial space where it is then anchored or placed in contact with the heart.

Still further in accordance with the present invention, there is provided a transthoracic method for injecting a substance or introducing a working apparatus (e.g., electrode, sensor, etc.) into the heart. In this method, an opening (e.g., a needle puncture) is formed in the chest wall and a tissue penetrating catheter is advanced through that opening, through the pericardium and into the pericardial space. The penetrating catheter comprises i) an elongate catheter body, ii) a hollow tissue penertator advanceable from the catheter body and iii) an orientation element useable to pre-determine the specific trajectory or direction in which the penetration will advance from the catheter body. The catheter's orientation element is then used to position and orient the catheter such that when the penetration is subsequently advanced from the catheter, the penetration will penetrate into the heart (e.g., to a subepicardial target location in the myocardium, coronary vessel, coronary sinus or chamber of the heart). After the catheter has been so positioned and oriented, the penetration is advanced from the catheter and into the target location within the heart. Thereafter, a substance is delivered or a working apparatus (e.g., a guidewire, electrode, etc.) is advanced through the hollow penetration and into the target location within the heart.

Further objects and advantages will become apparent to those of skill in the art upon reading and considering the following detailed description and the accompanying figures to which it refers.

BRIEF DESCRIPTION OF THE DRAWINGS

FIGS. 3a-3d show steps in a method for transluminal placement of a guidewire into the pericardial space.

DETAILED DESCRIPTION

Applicant has previously issued patents and filed patent applications that describe the use of image-guided penetration catheters for the introduction of apparatus, such as pacing leads or other electrodes, to target locations within tissues or organs. These prior patents and patent applications include U.S. Pat. Nos. 5,830,222, 6,068,638 and 6,071,292 or copending U.S. patent application Ser. Nos. 08/730,327, 09/056,589, 09/282,276 and 09/282,774. In general, the image-guided penetrating catheter comprises an elongate, flexible catheter body, a tissue penetrator advanceable from the catheter body and an orientation element useable to pre-determine the specific trajectory or direction in which the penetration will advance from the catheter body. The orientation element may comprise imageable marking(s), sensor(s), imaging transducer(s), electro-anatomical mapping and catheter guidance system(s) or any other suitable type of apparatus or system useable to predict the direction or track on which the penetration will advance from the catheter body, including but not necessarily limited to those described in U.S. Pat. Nos. 5,830,222, 6,068,638 and 6,071,292 and published PCT International Patent Application Nos. PCT/US99/07115, PCT/US99/07112 and unpublished United States-designating PCT International Patent Application No. PCT/US02/03941, the entirety of each such patent or patent application being expressly incorporated herein by reference. One such guided tissue penetrating catheter is available as the Crosspoint® Transaccess® catheter from TransVascular, Inc. of Menlo park, Calif.

After the catheter body has been positioned in a vessel or body conduit near the target location, the operator uses the orientation element to place the catheter body in a specific longitudinal position and a specific rotational orientation prior to advancement of the penetration from the catheter body. Such specific positioning and orientation of the catheter body ensures that when the penetration is subsequently advanced, the penetration will enter the desired target location.

Accompanying FIGS. 1-10c illustrate various examples of devices and methods of the present invention.

Figure 1A:
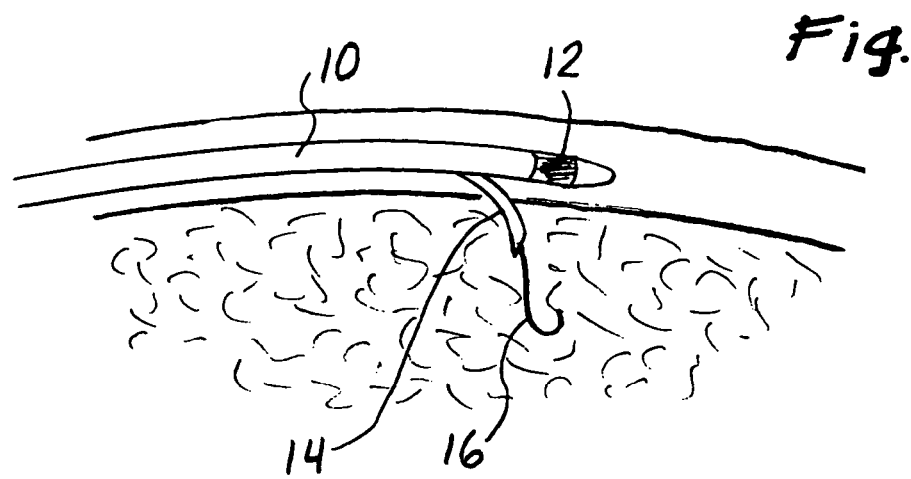
FIGS. 1a-1c show several steps in a method wherein a guided tissue penetrating catheter is used to form an interstitial penetration tract into which an indwelling interstitial electrode is implanted such that the electrode remains in place after the penetrating catheter has been removed.
Figure 1B:
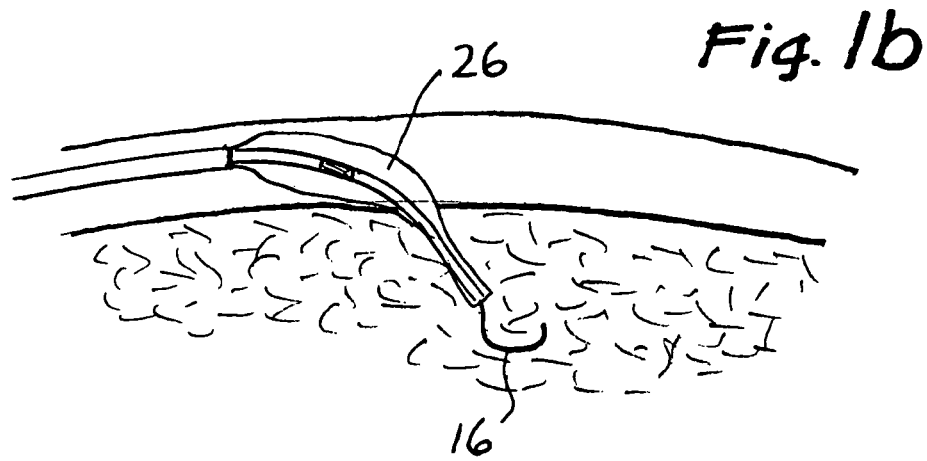
Figure 1C:
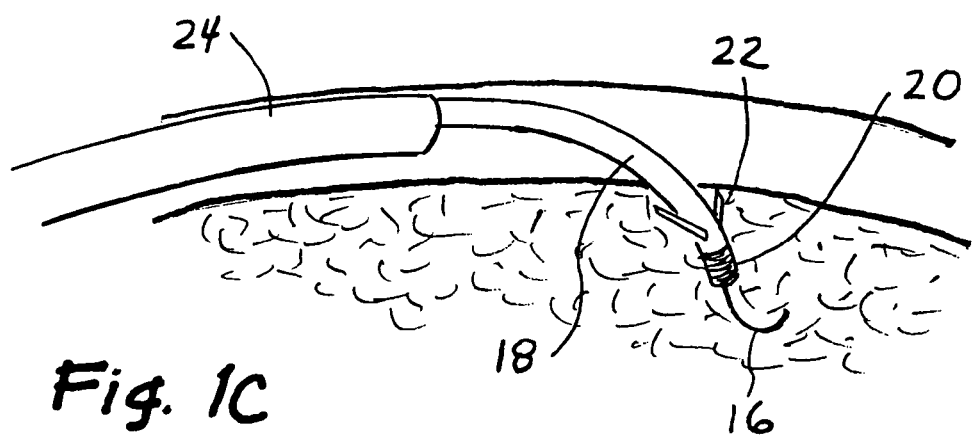

FIGS. 1a-1c show one method by which a guided penetrating catheter 10 may be used to implant an electrode 20, or other device at an interstitial location that is adjacent to or a spaced distance from the lumen of a blood vessel or body cavity into which the catheter 10 is inserted. As shown, in this example, the penetrating catheter 10 may be positioned in a blood vessel (e.g., a coronary blood vessel, coronary sinus, atrium of the heart or any other vessel or cavity within the body) and the target zone or area may be located within tissue (e.g., myocardium, brain, spinal canal, vascular space, etc.) adjacent to or a spaced distance outside of the blood vessel. This may be accomplished in any suitable manner. In some embodiments, it will be desirable to position the catheter 10 in a coronary vein or in the coronary sinus. In such embodiments, a coronary sinus guide catheter and/or subselective sheath as described in published PCT International Patent Application No. PCT/US99/07115 and copending U.S. patent application Ser. No. 09/282,276 may be used to facilitate advancement of the penetrating catheter 10 into the coronary venous vasculature such that a penetrator 14 may be advanced from the catheter 10 to a desired location within the myocardium.

The penetrator 14 may comprise a hollow member such as a needle through which, in some applications, a guidewire 16, electrode 20, pacing lead/electrode 18/20 or other apparatus may be advanced into and implanted in the target location. In applications such as that shown in FIGS. 1a-1c, a penetrating catheter 10 of the above-summarized character, having a hollow needle penetrator 14, is inserted into the coronary vasculature and used to implant a pacing lead 18 and electrode 20 within myocardial tissue located adjacent to or a spaced distance from a coronary blood vessel of a human or veterinary patient. Although this example relates to intramyocardial pacing lead placement, this same apparatus and technique may be used to implant other types of electrodes and other apparatus in organs or tissues, other than the myocardium. In this example, the penetrating catheter body is inserted into the vasculature (e.g., into the subclavian or jugular vein) of a human or veterinary patient and advanced into a coronary blood vessel (e.g., a coronary vein adjacent to the site of the intended pacing electrode implantation). As shown in FIG. 1a, the penetrating catheter's orientation element 12 is then used to position and orient the catheter body 10 such that, when the penetrator 14 is subsequently advanced from the catheter body 10, the penetrator 14 will penetrate through the wall of the blood vessel coronary blood vessel and into the myocardium to an intramyocardial location where it is desired to implant or position a pacing electrode 20.

Once the penetrator 14 has been advanced from the catheter 10 and into the myocardium, the operator may proceed with implantation or positioning of a desired type of electrode in several different ways. One way, shown in FIGS. 1b and 1c, involves a) advancement of a guidewire 16 through the lumen of the penetrator 14 and into the myocardium, b) withdrawal of the penetrator 14 back into the catheter 10, c) removal of the catheter 10, d) optional dilation or enlargement of the myocardial tract surrounding the guidewire 16 (if necessary) and e) subsequent advancement of an electrode 20 and lead 18 over the guidewire 16 such that the electrode 20 becomes embedded within the myocardial tissue. The pacing lead 18 extends through the patient's vasculature and is connected to a pacing device which sends the desired pacing signals through the pacing lead 18 to the intramyocardially implanted pacing electrode 20. Such pacing device is preferably implanted subcutaneously but may comprise an extracorporeal device located on or near the patient's body. In at least some embodiments, the pacing electrode 20 is configured and implanted such that it may subsequently be removed by pulling in the proximal direction on the pacing lead. In this regard, flexible barbs 22 may be provided on the pacing lead 18 to engage the adjacent myocardial tissue and to hold the electrode 20 in place. When it is desired to remove the pacing electrode 20, the operator may pull on the pacing lead 18 with sufficient force to cause the flexible barbs 22 to bend or evert and allowing the electrode 20 to be extracted and removed. By inserting the electrode into the target tissue as apposed to leaving it in the vascular space, it may be possible to decrease the size of the electrode itself because of the higher current density and lower impedance interface.

As shown in the accompanying FIGS. 1a and 1b, in some applications of the invention, a guidewire 16 may be inserted through the lumen of the penetrator 14 and into the myocardial tissue. Thereafter, the penetrator 14 may be retracted into the catheter 10 and the catheter 10 may be removed, leaving the guidewire 16 in place. Thereafter, as shown in FIG. 3, a pacing lead/electrode assembly 18/20 having a guidewire lumen extending therethrough, is advanced over the previously inserted guidewire and into the myocardium. In at least some applications, a tubular catheter or sheath 24 may be advanced over the guidewire 16 to a position within the coronary vasculature and the electrode lead/electrode assembly 18/20 may then be advanced through the sheath 24, over the guidewire 16 and into the desired position within the myocardial tissue.

As shown in FIG. 1b, in some applications, it will be desirable to enlarge (dilate, expand, stretch, debulk, cut, etc) the intramyocardial tract created by advancement of the penertator 14 and or guidewire 16 before passing the electrode 20 into that tract. This may be accomplished by initially advancing a guidewire 16 through the penetrator 14 as shown in FIG. 1 and described above. Thereafter, the penetrator 14 may be retracted into the catheter 10 and the catheter 10 may be removed, leaving the guidewire 16 in place. Thereafter, as shown in FIG. 2, a tract enlarging apparatus 26 is advanced over the guidewire 16 and used to enlarge the intramyocardial tract surrounding the guidewire 14. Thereafter, the tract enlarging apparatus is removed and the as shown in FIG. 3, a pacing lead/electrode assembly 18/20 having a guidewire lumen extending therethrough, is advanced over the previously inserted guidewire and into the myocardium. In at least some applications, a tubular catheter or sheath 24 may be advanced over the guidewire 16 to a position within the coronary vasculature and the electrode lead/electrode assembly 18/20 may then be advanced through the sheath 24, over the guidewire 16 and into the desired position within the myocardial tissue.

The tract enlarging apparatus 26 may be a balloon catheter, such as a standard angioplasty catheter, and the balloon may be inflated within the tract to dilate the surrounding myocardial tissue. Alternatively, the tract enlarging apparatus may comprise an electrosurgical debulking device, tissue cutting device or other suitable channel enlarging device, examples of which are described in U.S. Pat. Nos. 6,190,353, 5,830,222, 6,283,983 and 6,068,638 as well as Published PCT International Patent Application Serial No. PCT/US99/07519 entitled Devices, Systems And Methods For Enlarging Anatomical Passageways Or Interstitial Puncture Tracts, the entireties of which are expressly incorporated herein by reference.

FIGS. 2a-10c show additional aspects and examples of the present invention. For example, in FIG. 2a, the penetrating catheter 10 is advanced into a body lumen, the orientation element 12 is then used to position and orient the catheter body 10 within the body lumen such that, when the penetrator 14 is subsequently advanced from the catheter body 10, the penetrator 14 will penetrate through the wall of the body lumen and to a target interstitial location within tissue located outside the body lumen. An electrode 20 a is incorporated in or positioned on or in the penetrator 14. The catheter 10 remains in the body lumen and the penetrator 14 remains inserted through the wall of the body lumen and into the myocardium or other target tissue, so long as it is desired to have the electrode 20a so positioned. When it is desired to remove the electrode, the penetrator 14 with its accompanying electrode 20a are withdrawn into the catheter 10 and the catheter 10 is removed. Optionally, anchoring members may be formed on the penetrator 14 to deter its accidental withdrawal from the tissue or an anchoring member, such as an anchoring guidewire 42 may be passed through the lumen of the penetrator 14 and into the tissue distal to the penetration tip. Such anchoring guidewire 42 has a curved or expandable tip configuration which, when it emerges out of the distal end of the penetrator 14 lumen assumes a curved configuration or expands such that it anchors into the surrounding tissue and helps to deter unwanted dislodgement or withdrawal of the penetrator 14, electrode 20a and/or catheter 10.

When it is desired to remove the penetrator 14, electrode 20a and/or catheter 10 the anchoring guidewire 42 is withdrawn into the lumen of the penetration, thereby eliminating the anchoring effect and allowing the penetrator 14 with its accompanying electrode 20a to be withdrawn into the catheter 10 and the catheter 10 to be removed.

Figure 2A:
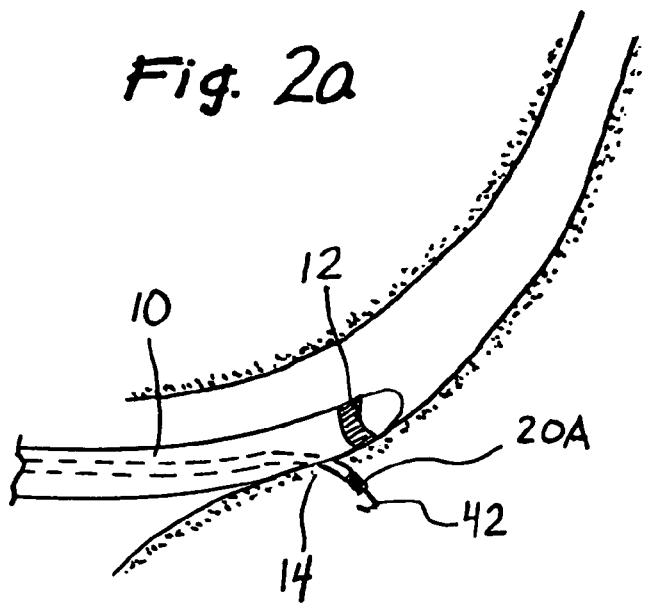
FIGS. 2a-2b show steps in a method wherein a penetration needle is advanced from a guided tissue penetrating catheter into adjacent tissue and an electrode is included in or advanced through the needle such that the electrode is positioned within the tissue while the penetrating catheter remains in place.
Figure 2B:
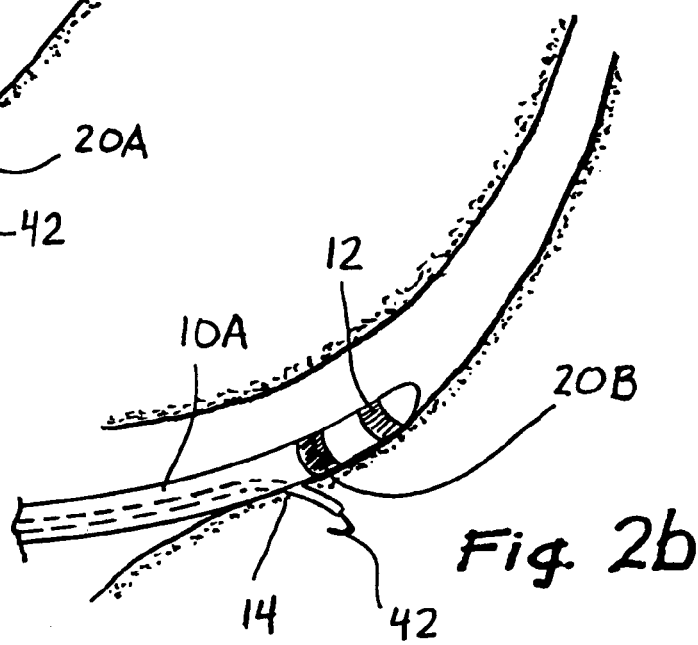

FIG. 2b shows another example wherein the electrode 20b is actually located on the penetrating catheter 10a and the penetrator 14 and anchoring member 42 are used to pull the electrode 20b into firm abutting contact with the wall of the blood vessel or other body lumen within which the catheter 10a is positioned. Thus, in this embodiment, the electrode 20b does not actually become interstitially implanted within tissue, but rather is held in abutting contact with the wall of the blood vessel or other body lumen in which the catheter 10a is positioned.

Figure 3A:
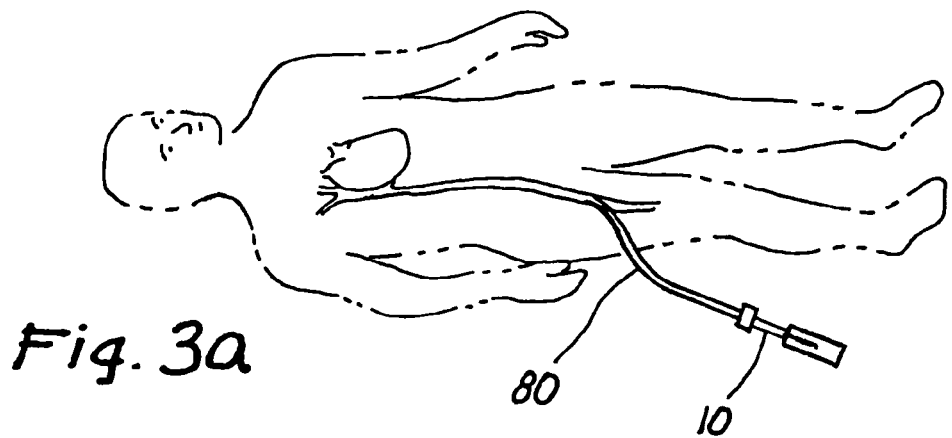

FIGS. 3a-3d show an alternative approach wherein a penetrating catheter 10 is percutaneously inserted into the patient's vasculature (e.g., by femoral venipuncture) and advanced into the coronary venous sinus CS (or into any other suitable cardiac location such as a coronary vein, coronary artery, atrium or other chamber of the heart) and the penetrator 14 is advanced from the catheter 10 into the pericardial space PCS. A guidewire GW is then advanced trough the lumen of the penetrator 14 and into the pericardial space PCS, as shown in FIG. 3c. Thereafter, the penetrator 14 is retracted back into the catheter 10 and the catheter 10 is removed, leaving the distal portion of the guidewire in the pericardial space, as shown in FIG. 3d. In at least some embodiments, the tissue surrounding the penetration tract created by the penetrator 14 will seal or close around the guidewire GW (or around any pacer lead or other item that remains positioned within the tract after the penetrator 14 is withdrawn), thereby minimizing or preventing leakage trough the tract. At this point, the operator may proceed in several ways, examples of which are shown in FIGS. 4a & 4b and 5a & 5b, respectively.

Figure 4A:
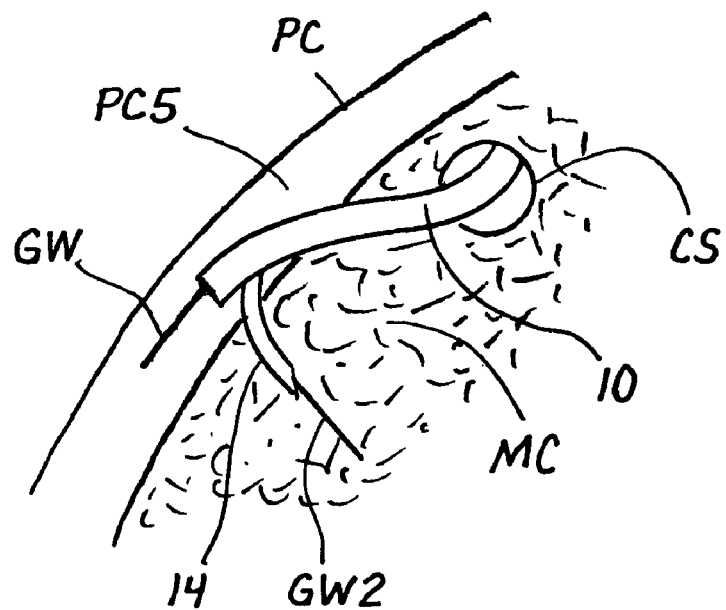
FIG. 4a shows a guided tissue penetrating catheter advanced over the guidewire that was placed in the pericardial space in FIGS. 3a-3d and used to penetrate from the pericardial space to a subepicardial target location (e.g., a location within myocardium, the lumen of a coronary vessel, a chamber of the heart, etc.) and for introduction of a second guidewire to that subepicardial target location.
Figure 4B:
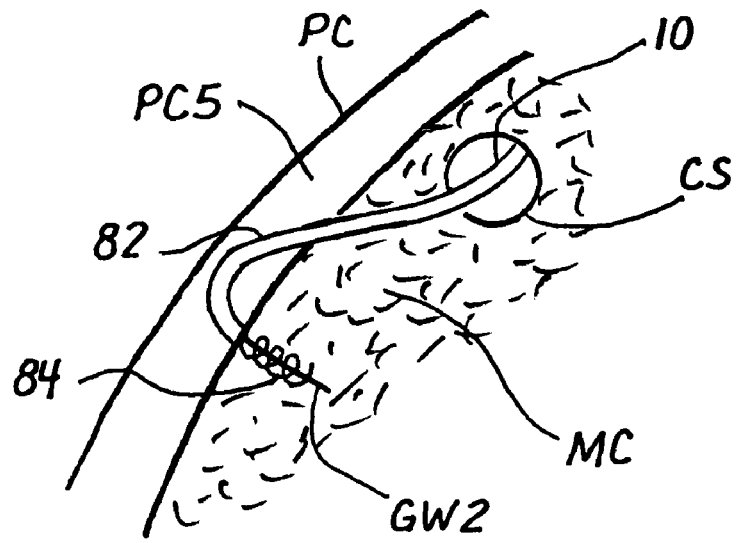
FIG. 4b shows an electrode advanced over the second guidewire that was placed in FIG. 4a and anchored to the myocardium by an electrode anchoring element.

In the procedure shown in FIGS. 4a & 4b, the penetrating catheter is reinserted and advanced over the previously positioned guidewire GW so that the distal end of the penetrating catheter 10 enters the pericardial space PCS. The penetrating catheter's orientation element 12 is then used to position and rotationally orient the catheter 10 such that, when the penetrator 14 is subsequently advanced from the catheter body 10, the penetrator 14 will penetrate into the myocardium MC to a desired penetration target site or to a desired depth below the epicardial surface and a second guidewire GW2 is advanced through the lumen of the penetrator 14 and into the myocardium MC, as shown in FIG. 4a. Thereafter, the penetrator 14 is once again retracted back into the catheter 10 and the catheter 10 is once again removed, leaving the distal portion of the second guidewire GW2 in the myocardium and the remainder of that second guidewire GW2 extending outwardly through the pericardial space, through the coronary sinus CS and back to the original catheter insertion site. Thereafter, a tubular electrode device 82 is advanced over the second guidewire. Then, as shown in FIG. 4b, an anchoring member 84 on the distal end of the electrode device 82 is advanced into the myocardium MC such that it frictionally engages the myocardium so as to hold a contact electrode 83 on the distal end of the electrode device 82 in contact with the myocardium and/or epicardial surface of the heart. The second guidewire GW2 may then be removed, leaving the electrode device 82 in place.

Figure 5A:
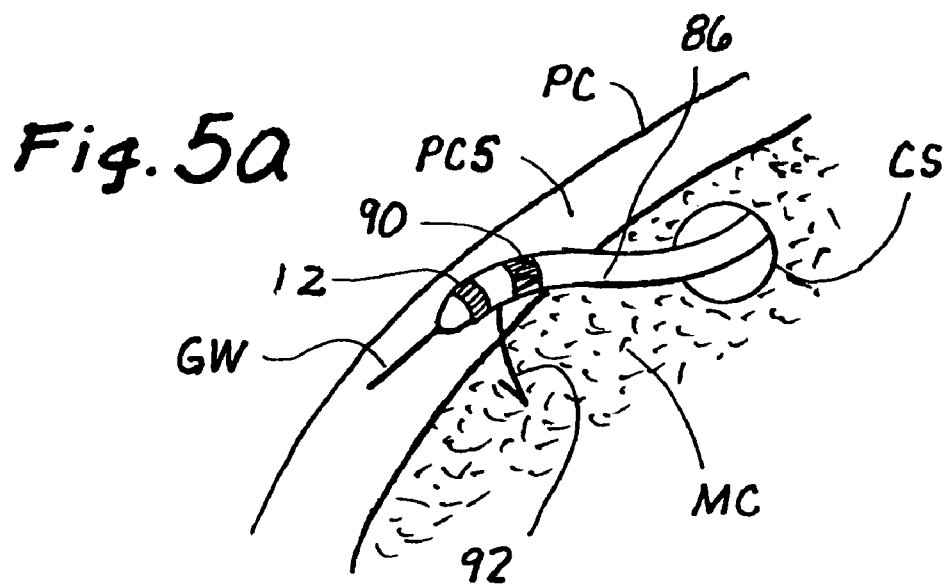
FIG. 5a shows a guided electrode catheter device of the present invention that is equipped with a guidance sensor, an electrode and a laterally deployable anchoring element, wherein the guided electrode catheter device has been advanced over the second guidewire that was placed in FIG. 4a and anchored to the myocardium by the laterally deployable electrode anchoring element.
Figure 5B:
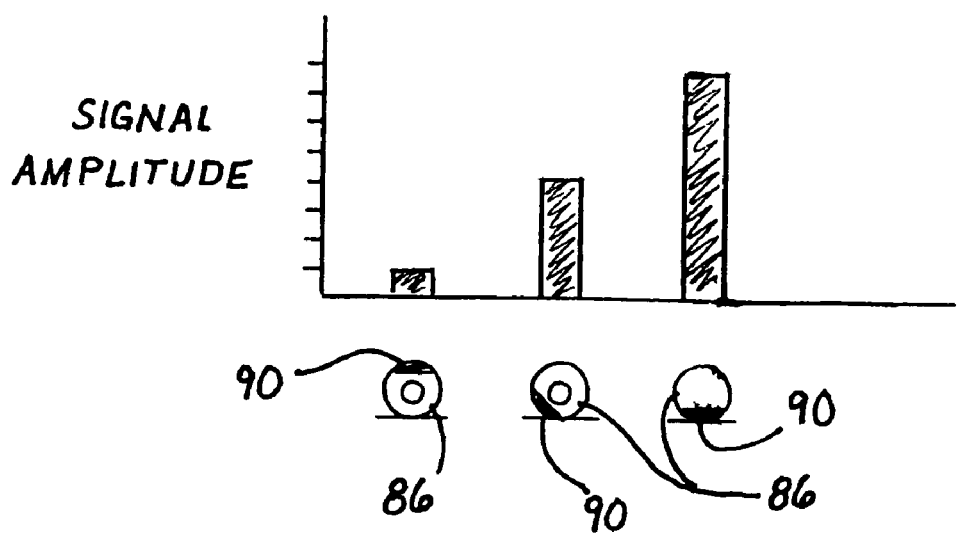
FIG. 5b is a graphic showing of the changes in signal amplitude received from the guidance sensor of the guided electrode catheter device of FIG. 5a when the catheter body is in various rotational orientations relative to the epicardial surface of the heart.

Another approach is shown in FIGS. 5a and 5b. In this approach, the guidewire GW has previously been advanced into the pericardial space PCS as shown in FIG. 3d. A tubular electrode device 86 is then advanced over the guidewire GW and into the pericardial space, as shown in FIG. 5a. This electrode device comprises an anchoring member 92 that is laterally advanceable from the device 86 so as to enter and frictionally engage the myocardium MC and a contact electrode 90 that is located on the outer surface of the device 86. Optionally, some embodiments of this electrode device 86 may also have a catheter orientation element 12 of a type previously described above and/or in the incorporated prior patents and patent applications with respect to the penetrating catheters 10, 10a.

In some embodiments of this device 86, such as those that do not include another type of catheter orientation element 12, the contact electrode 90 may be positioned at a specific radial location on the body of the device 86 that corresponds to the direction in which the anchoring member 92 will extend from the device 86 and such electrode 90 may be alternately useable as a sensing electrode and as a signal emitting electrode. The electrode 90 may initially be used in sensing mode to sense impedance or receive an electrophysiological signal (e.g., electrocardiogram) from the myocardium MC, such that the impendence or sensed electrophysiological signal (e.g., ECG) is highest in amplitude when the anchoring member 92 is directed toward the myocardium. In this manner, the operator may rotate the body of the device 86 within the pericardial space until the impedance or received signal amplitude peaks, thereby indicating that the device 86 is in its proper rotational orientation. Thereafter, the anchoring member 92 may be advanced into the myocardium MC and the contact electrode 90 will thus be held in juxtaposition or abutting contact with the myocardium or epicardium. After the device 86 has been so oriented and anchored, the electrode 90 may be changed to emitting mode and electrical cardiac pacing signals may be emitted by the electrode 90 into the heart. FIG. 5b shows a graphic example of the manner in which the sensed signal amplitude is peaked when the device 86 is oriented such that the electrode 90 is in contact with or is directed at the heart while the sensed signal amplitude is at its lowest when the device is rotated such that the electrode 90 (and this the anchoring member 92) is on the side of the device that is away from the heart.

Figure 6A:
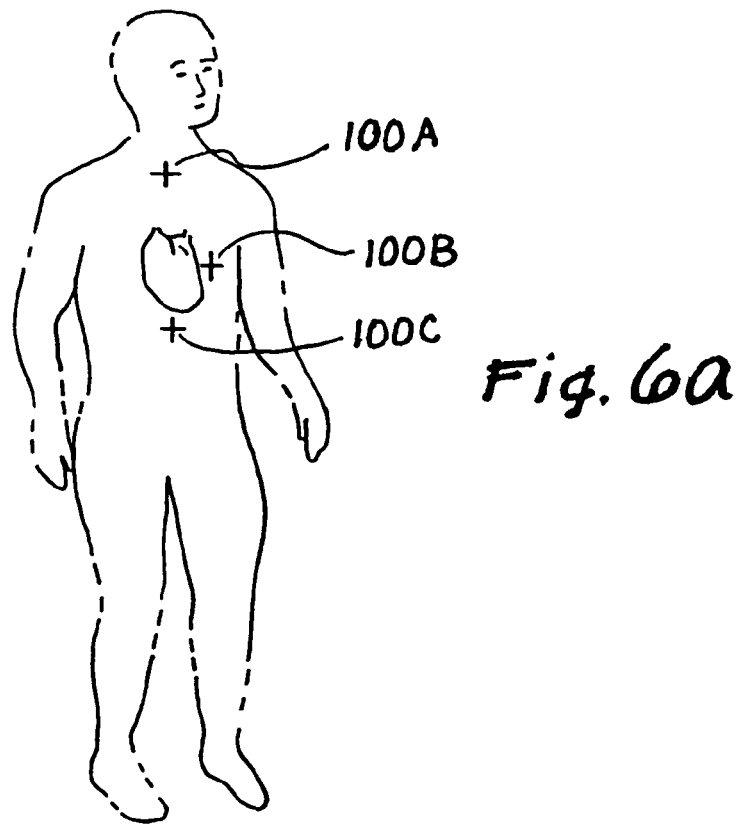
FIG. 6a is a schematic showing of a human patient illustrating suprasternal, intracostal and subxyphoid locations at which a guided tissue penetrating catheter may be inserted through the chest wall to gain access to the pericardial space for placement of an electrode or other device, delivery of a substance, etc.
Figure 6B:
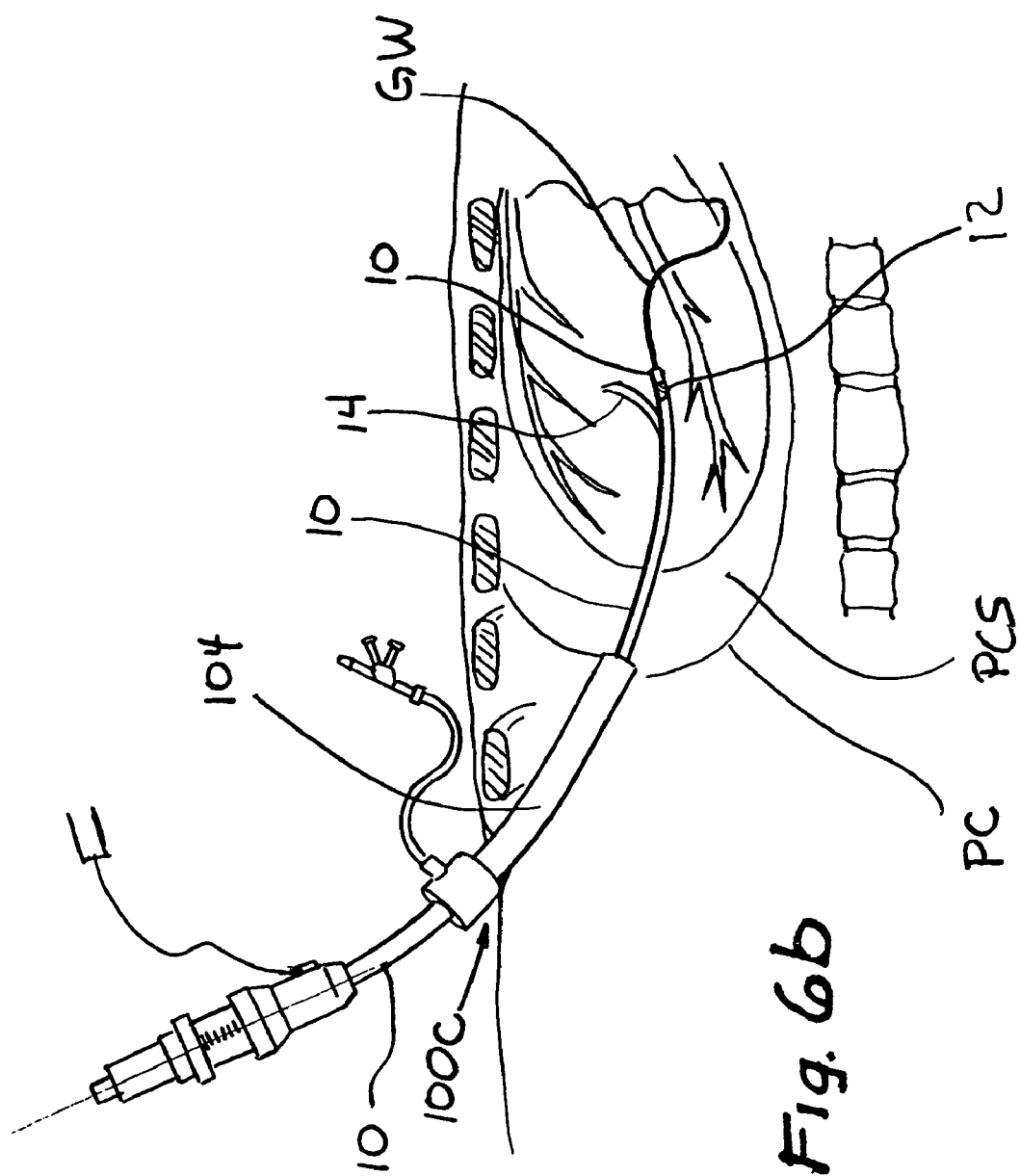
FIG. 6b is a longitudinal sectional view of the thorax of a human patient with a guided tissue penetrating catheter inserted through a subxyphoid entry site into the pericardial space and wherein a penetration has been advanced from the guided tissue penetrating catheter to a subepicardial target location (e.g., a location within myocardium, the lumen of a coronary vessel, a chamber of the heart, etc.) to facilitate advancement of a guidewire, electrode, other device or delivery of a substance to an endoepicardial or subepicardial target location.
Figure 7A:
FIGS. 7a-7j are side views of various types of electrode anchoring elements that may be used to anchor electrodes within the hear in accordance with this invention.
Figure 7B:
Figure 7C:
Figure 7D:
Figure 7E:
Figure 7F:
Figure 7G:
Figure 7H:
Figure 7I:
Figure 7J:
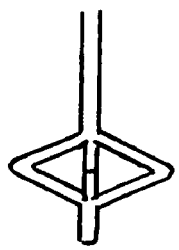

FIGS. 6a and 6b show an example of a transthoracic approach to placement of an electrode or other apparatus, or injection of a substance, into the heart. In this example, an opening, such as a needle penetration, is made though chest wall at a desired site such as a suprasternal site 100a, an intercostal site 100b or a subxyphoid site 100c. Thereafter, as shown in FIG. 6b, a sheath 104 is inserted through the opening and through the pericardium PC into the pericardial space PCS. Thereafter, a tissue penetrating catheter 10, as described above, is inserted through the sheath 104 and into the pericardial space PCS. In some applications, a guidewire GW may be initially advanced through the sheath 104 and into the pericardial space PCS and the catheter 10 may then be advanced over the guidewire GW. The catheter orientation element 12 is then used to position and orient the catheter 10 within the pericardial space PCS such that when the penetrator 14 is subsequently advanced from the catheter 10 the penetrator 14 will enter some desired target location within the heart. Typically, this desired location will be beneath the epicardium (a "sub-epicardial target location"). In some applications the desired target location will be within myocardial tissue, such as an intra-myocardial site to which is it desired to deliver a substance and/or device (e.g., a pacing or ablation electrode). In other applications, the desired target location may be within the lumen of a coronary blood vessel, coronary sinus or chamber of the heart (e.g., ventricle, atrium) into which it is desired to deliver a substance or device (e.g., pacing or ablation electrode). After the catheter has been positioned and oriented, the penetrator 14 is advanced from the catheter, and into the desired target location. Thereafter, a substance may be injected though the hollow penetrator 14 or a device (e.g., guidewire, pacing electrode, ablation electrode, sensor, etc.) may be advanced through the hollow penetrator 14 and into the target location. In some applications, a second guidewire may be advanced through the penetrator 14 and into the heart. Thereafter, the penetration may be retracted into the catheter 10 and the catheter 10 may be withdrawn, leaving the second guidewire in place. Thereafter, electrodes (or other devices) such as those shown in FIGS. 2a-2b and 4b and described in detail above, may be advanced over that second guidewire and positioned in and/or anchored to the heart.

FIGS. 7a-7j shows a number of examples of anchoring tips that may be formed on the penetrator 14 or anchoring guidewire 42 or electrode lead 18 to anchor it into the myocardium or other tissue. It will be appreciates that the showings of FIGS. 7a-7j are merely examples, and numerous other types of anchoring tip designs may be possible and useable in this invention.

Figure 8:
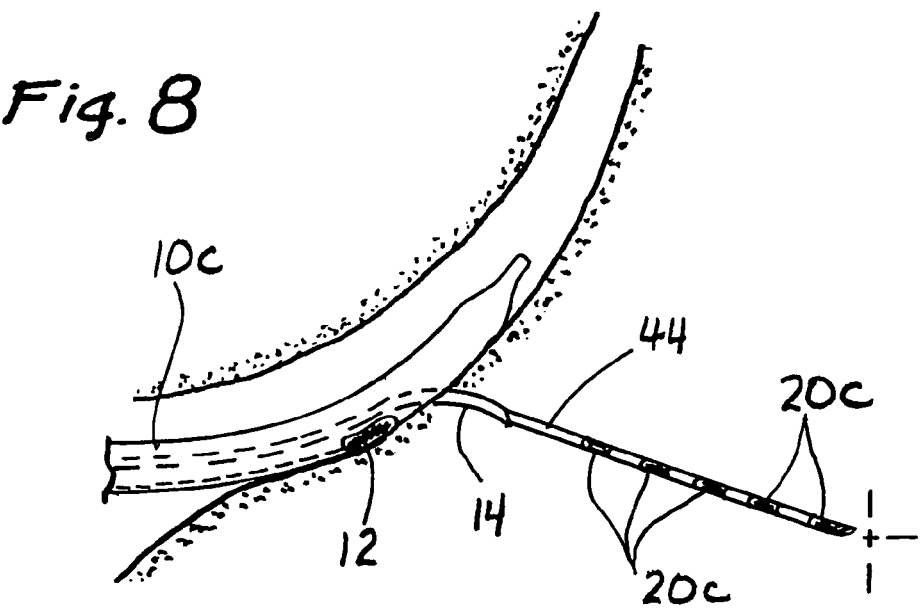
FIG. 8 shows a guided tissue penetrating catheter positioned within a vessel (e.g., coronary artery, coronary vein, coronary sinus) with its penetration advanced into adjacent tissue (e.g., myocardium) and a microlead having a plurality of electrodes thereon advanced through the lumen of the penetration into the tissue.

FIG. 8 shows another example wherein a penetrating catheter 10c is positioned within a blood vessel or other body lumen and the orientation element 12 is used to position and rotationally orient the catheter 10c within the body lumen such that subsequent advancement of the penetrator 14 will cause the penetration to advance on a trajectory or path toward an interstitial target location TL. After the catheter 10c has been so positioned and oriented within the body lumen, the penetrator 14 is advanced on a track toward the target location TL. Thereafter, a microlead 44 having one or more electrodes 20c thereon is advanced through the lumen of the penetrator 14 and further in the general direction of the target location TL. Thereafter, the penetrator 14 may be withdraw into the catheter 10c and the catheter 10c may be removed, leaving just the microlead 44 and electrode(s) 20c in place. In some applications all of the electrodes may be actuated or fired simultaneously, in series or in any desired combination(s) or pattern(s). In other applications, each electrode 20c may be actuated or fired independently and a response to such electrode firing may be monitored. On this basis, the operator my determine which one or ones of the electrode(s) 20 is/are optimally positioned to cause the desired response and, thereafter, that selected electrode(s) may be used to cause the desired response.

Figure 9A:
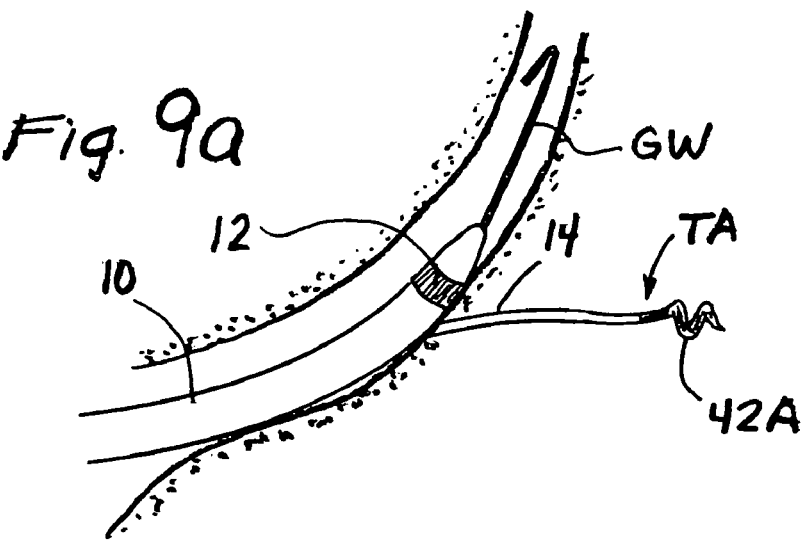
FIGS. 9a-9c show steps in a method wherein a guided tissue penetrating catheter, anchorable guidewire and balloon catheter are used for transluminal placement of a radially expandable interstitial electrode.
Figure 9B:
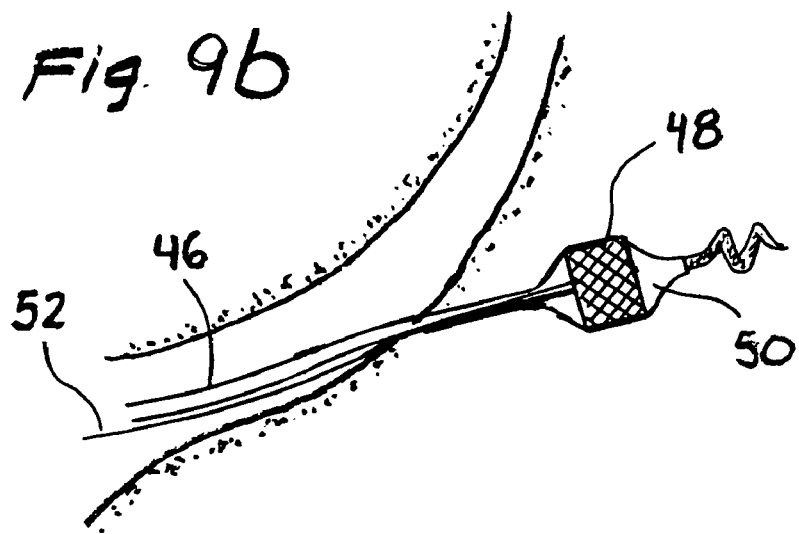
Figure 9C:
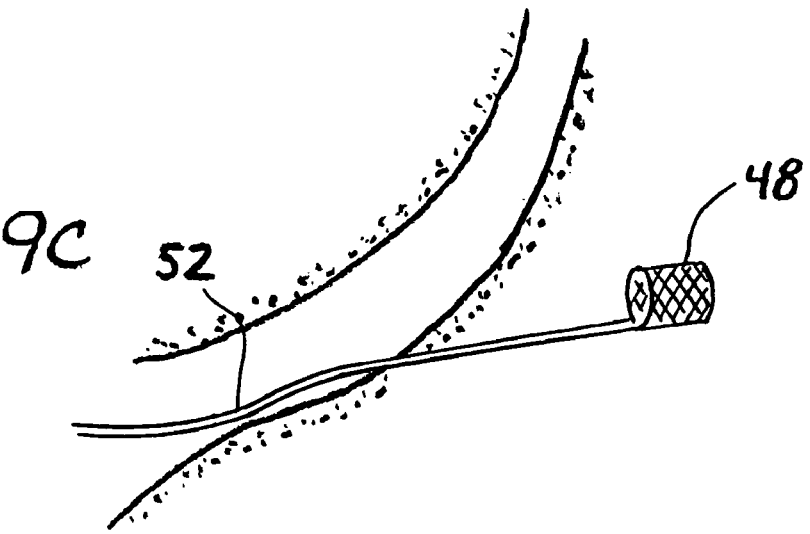

FIGS. 9a-9c show another example of the present invention wherein an expandable electrode is implanted within tissue located outside of a blood vessel or other anatomical conduit. As shown in FIG. 9a, a penetrating catheter 10 is inserted into the vasculature (e.g., into the subclavian or jugular vein) of a human or veterinary patient and advanced into a coronary blood vessel (e.g., a coronary vein adjacent to the site of the intended pacing electrode implantation). The penetrating catheter's orientation element 12 is then used to position and orient the catheter body 10 such that, when the penetrator 14 is subsequently advanced from the catheter body 10, the penetrator 14 will penetrate through the wall of the blood vessel or anatomical conduit and into the target area TA where it is desired to implant an electrode. An anchoring guidewire having a resilient distal end that is biased to a helical configuration 42a is then advanced through the lumen of the penetrator 14 and into tissue located within or directly beyond the target area TA. As the distal end of this guidewire 42a emerges out of the lumen of the penetrator 14, it will assume its helical configuration, thereby resisting proximally directed pull-out of the guidewire 42a. The penetrator 14 is then retracted into the penetrating catheter 10 and the penetrating catheter 10 is removed, leaving the anchored guidewire 42a in place. Thereafter, a balloon catheter 45 having a balloon 50 and a radially expandable electrode member 48 positioned thereon is advanced over the guidewire 42a until the balloon 50 and electrode 48 are positioned within the target area TA. As shown in FIG. 9b, the balloon 50 is then inflated causing the electrode 48 to expand to a configuration that resists pull out from the surrounding tissue. As shown in FIG. 9c, the balloon 50 is then deflated, the anchoring member or guidewire 42a is retracted into the balloon catheter 46 and the balloon catheter 46 is removed, leaving the expanded electrode 48 and its attached lead 52 in place. It will be appreciated that other expansion apparatus (e.g., expandable mechanical devices, expandable mesh cages or radially expandable members) mY be used instead of a balloon. Also, it will be appreciated that in some embodiments the electrode may be self-expanding rather than pressure-expandable. (e.g., formed of resilient self-expanding material, shape memory material such as NiTi alloy, swellable material such as a hydrogel or hydrophilic polymer, etc.) The expandable electrode may remain implanted indefinitely or may be formed at least partially of resorbable or biodegradable material that resorbs or undergoes biodegredation over time, such as polylactic acid or the like. In this regard, if non-conductive resorbable or biodegradable materials are used, conductive elements (e.g., wires, metal powder, etc) may be incorporated into or mounted on the biodegradable portion of the electrode 48 to provide the desired electrical transmission. In some embodiments, the lead lead 52 may extend into or on the expandable electrode member 48 to provide the desired electrical conduction. Such wire may be detachable from the expandable electrode member 48 and thus removable from the body. Or, the expandable electrode member 48 may biodegrade over a prescribed time period and then the lead 52 may be extracted and removed.

Figure 10A:
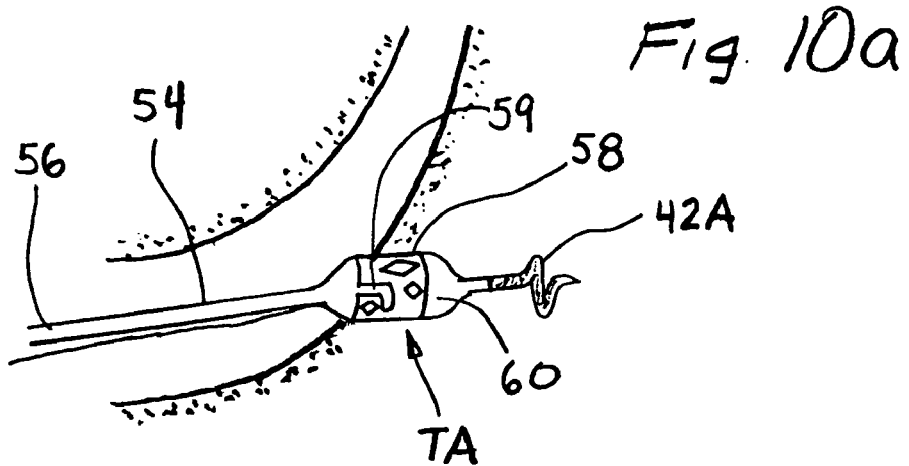
FIGS. 10a-10c show steps in another method wherein a radially expandable electrode anchor is implanted at an interstitial location using an anchorable guidewire that has previously been placed by a guided tissue penetrating catheter and also using a balloon catheter for expanding a portion of the radially expandable electrode anchor.
Figure 10B:
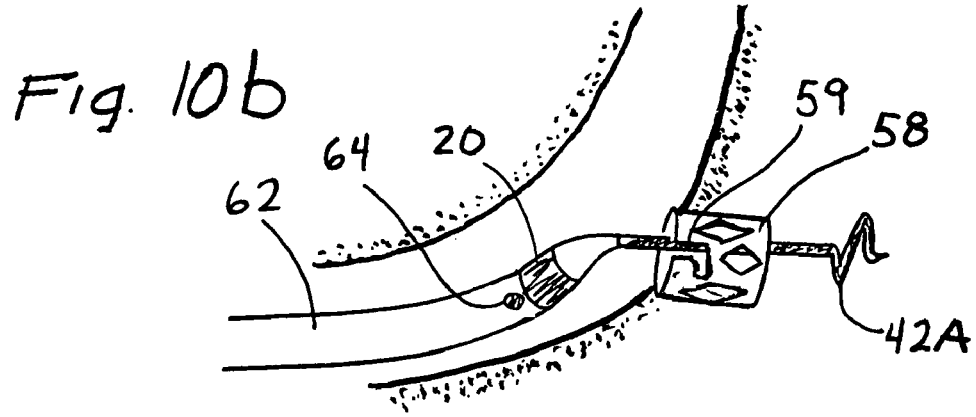
Figure 10C:
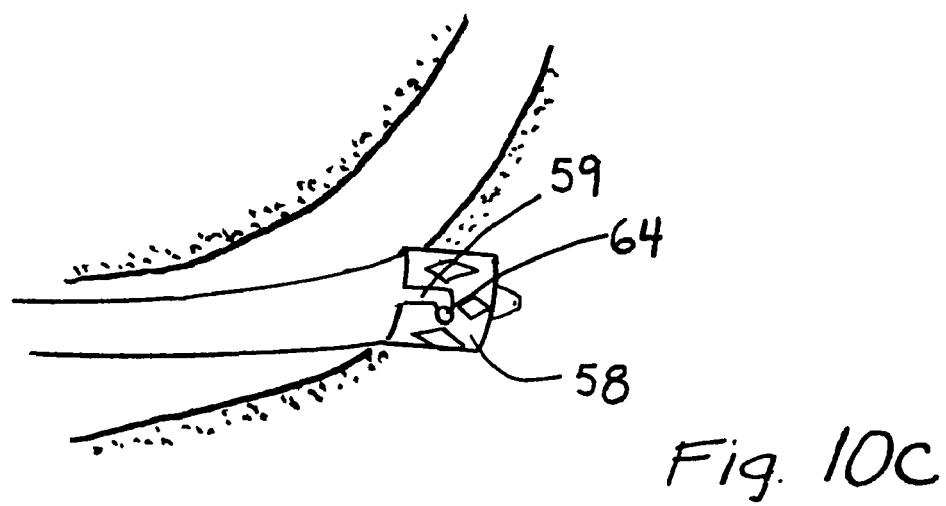

FIGS. 10a-10c show yet another example of a method and apparatus of the present invention, in this example, an expandable anchoring member 58 is implanted in tissue outside the lumen of the blood vessel or anatomical conduit and a separate catheter-mounted electrode 20 is inserted into and engaged with such anchoring member. In this example, a penetrating catheter 10 is initially used in the manner shown in FIG. 9a and described above to place an anchorable guidewire 42a in a target area. Thereafter, the penetrator 14 is then retracted into the penetrating catheter 10 and the penetrating catheter 10 is removed, leaving the anchored guidewire 42a in place. Thereafter, a balloon catheter 56 having a balloon 60 and a radially expandable anchoring member 58 positioned thereon is advanced over the guidewire 42a until the balloon 50 and anchoring member 58 are positioned within the target area TA. Thereafter, as shown in FIG. 10b, the balloon is inflated causing the anchoring member 58 to become expanded and implanted with the tissue of the target area TA. The balloon 60 is then deflated and the balloon catheter 54 is removed, leaving the expanded anchoring member 58 and anchored guidewire 42a in place. It will be appreciated that other expansion apparatus (e.g., expandable mechanical devices, expandable mesh cages or radially expandable members) may be used instead of a balloon. Also, it will be appreciated that in some embodiments the electrode anchor 58 may be self-expanding rather than pressure-expandable. (e.g., formed of resilient self-expanding material, shape memory material such as NiTi alloy, swellable material such as a hydrogel or hydrophilic polymer, etc.) Thereafter, an elongate electrode member such as a small catheter 62 having an electrode 20 positioned thereon is advanced over the anchoring guidewire 42 and into the expanded anchoring member 58. A projection 64 on the electrode catheter 62 advances into an L shaped slot 59 on the anchoring member 58, as shown in FIG. 10b. Thereafter, as shown in FIG. 10c, the electrode catheter 62 is rotated, causing the projection 64 to seat within the sidearm of the L shaped slot, as shown. Such seating of the projection 64 within the slot 59 of the anchoring member 64 resists proximal pull out of the electrode catheter and holds the electrode 20 in a desired position within the target area TA. When it is desired to remove the electrode catheter 62, the electrode catheter 62 is rotated in the counterclockwise direction, thereby causing the projection 59 to retract out of the side arm of the L shaped slot and allowing the electrode catheter 62 to be pulled back and removed. Optionally, the expandable anchoring member 58 may be formed of resorbable or biodegradable material such that it will resorb or biodegrade over a desired period of time.

Although the invention has been described above and in the accompanying drawings with reference to specific embodiments or examples, it is to be appreciated that many modifications, additions, deletions and alterations may be made to those examples without departing from the intended spirit and scope of the invention. It is intended that all such modifications, additions, deletions and alterations be included within the scope of the invention disclosed in this provisional patent application.

The invention claimed is:

1. A method for electrical stimulation of the heart of a human or animal subject, said method comprising the steps of:
    A) providing a penetration catheter that comprises an elongate flexible catheter body and a penetrator that has a hollow lumen, said penetrator being advanceable from a retracted position to an extended position;
    B) inserting the flexible penetration catheter body into the subject's vasculature, transluminally advancing the flexible catheter body through the subject's vasculature to a position within a coronary blood vessel;
    C) advancing the penetrator from the penetration catheter body positioned within a coronary blood vessel through a wall of the coronary blood vessel to a location within the pericardial space;
    D) advancing a first guidewire through the penetrator and into the pericardial space;
    E) retracting the penetrator and withdrawing the penetration catheter, leaving the first guidewire in the pericardial space;
    F) inserting the penetration catheter over the guidewire into the pericardial space;
    G) advancing the penetrator from the penetration catheter positioned in the pericardial space to create a penetration tract that extends from the pericardial space into the heart;
    H) advancing at least one electrode into the penetration tract; and
    I) actuating said at least one electrode to deliver electrical stimulation to the heart.

2. A method according to claim 1 wherein the penetrator advances laterally from the penetration catheter body inserted in Step B and wherein the penetration catheter further comprises an orientation element that is useable, while the penetrator is in its retracted position, to determine the lateral direction in which the penetrator will subsequently advance as it moves from its retracted position to its extended position, and wherein Step C comprises i) using the orientation element while the penetrator is in its retracted position to adjust the rotational orientation of the catheter body as needed to substantially ensure that subsequent movement of the penetrator to its extended position will cause penetrator to enter the desired location and ii) moving the penetrator from its retracted position to its extended position thereby causing the penetrator to penetrate to the desired location.

3. A method according to claim 1 wherein a single electrode is implanted.

4. A method according to claim 1 wherein a plurality of electrodes are implanted.

5. A method according to claim 4 wherein Step I comprises actuating a plurality of the electrodes simultaneously.

6. A method according to claim 4 wherein Step I comprises actuating a plurality of the electrodes separately.

7. A method according to claim 4, wherein the method further comprises:
   actuating each electrode separately and determining a response caused by the separate actuation of each electrode;
   selecting one or more electrodes that provide the most desirable response; and,
   thereafter actuating the selected one or more electrodes when it is desired to cause the response.

8. A method according to claim 4 wherein:
   the plurality of electrodes are positioned at spaced apart locations on a microlead and wherein Step H comprises advancing that microlead into a position within myocardial tissue; and
   Step I comprises i) actuating the electrodes independently and determining a response to the independent actuation of each electrode, ii) selecting the response that is most desirable and, thereafter, iii) actuating the electrode that caused the response that was selected as most desirable.

9. A method according to claim 1 wherein cardiac pacing signals are delivered in Step I.

10. A method according to claim 1 wherein the electrode is adapted to be anchored in tissue and wherein Step H further comprises anchoring the electrode.

11. A method according to claim 1 further comprising the step of retracting the penetrator to a retracted position within the penetration catheter that had been inserted in Step F, after the electrode has been implanted.

12. A method according to claim 11 further comprising the step of removing the penetration catheter that had been inserted in Step F.

13. A method according to claim 1 further comprising the step of injecting a substance through the penetrator lumen.

14. A method according to claim 1 wherein the electrode comprises an expandable electrode and wherein Step H further comprises expanding the electrode.

15. A method according to claim 1 wherein Step H comprises advancing a second guidewire though the penetrator of the penetration catheter positioned in the pericardial space and thereafter, advancing at least one electrode over that second guidewire.

* * * * *